United States Patent
Surina (10) Patent No.: US 7,493,232 B1
(45) Date of Patent: Feb. 17, 2009

(54) DEVICE AND METHOD FOR MONITORING HYDRATION STATUS

(76) Inventor: Blake J. Surina, 1021 Alameda Ave., Fircrest, WA (US) 98466

( * ) Notice: Subject to any disclaimer, the term of this patent is extended or adjusted under 35 U.S.C. 154(b) by 0 days.

(21) Appl. No.: 11/846,414

(22) Filed: Aug. 28, 2007

(51) Int. Cl.
G01C 22/00 (2006.01)
G06F 15/00 (2006.01)
G06F 19/00 (2006.01)
G01K 13/00 (2006.01)
A61B 5/00 (2006.01)

(52) U.S. Cl. .................. 702/160; 702/19; 702/127; 702/131; 600/307

(58) Field of Classification Search .......... 702/127, 702/131, 160, 19; 600/307
See application file for complete search history.

(56) References Cited

U.S. PATENT DOCUMENTS

| | | | |
|---|---|---|---|
| 4,066,068 A * | 1/1978 | Nilsson et al. | 600/307 |
| 4,566,461 A | 1/1986 | Lubell | |
| 5,387,164 A | 2/1995 | Brown, Jr. | |
| 6,013,009 A | 1/2000 | Karkanen | |
| 6,030,342 A | 2/2000 | Amano | |
| 6,138,079 A | 10/2000 | Putnam | |
| 6,241,684 B1 | 6/2001 | Amano | |
| 6,287,262 B1 | 9/2001 | Amano | |
| 6,475,158 B1 | 11/2002 | Orr | |
| 6,533,725 B1 * | 3/2003 | Endo et al. | 600/306 |
| 6,554,776 B1 | 4/2003 | Snow | |
| 6,675,041 B2 | 1/2004 | Dickinson | |
| 2002/0137992 A1 * | 9/2002 | Lahtinen | 600/307 |
| 2005/0070778 A1 | 3/2005 | Lackey | |
| 2006/0090765 A1 | 5/2006 | Surina | |
| 2007/0083092 A1 * | 4/2007 | Rippo et al. | 600/307 |

OTHER PUBLICATIONS

Astrand, P.O., and D. Rodahl, Textbook of Work Physiology: Physiological Bases of Exercise, McGraw Hill, 1977, pp. 376-377.

* cited by examiner

*Primary Examiner*—Eliseo Ramos Feliciano
*Assistant Examiner*—Janet L Suglo
(74) *Attorney, Agent, or Firm*—Christensen O'Connor Johnson Kindness PLLC (57) ABSTRACT

The invention relates to a device and method that provide an individualized guideline for fluid replacement during normal activity or inactivity. Preferred embodiments calculate the user's fluid loss using the equation: $\{[(\% \text{ humidity}^2 - 1600) * \text{time}]/J\} + [(\text{temp } °F. * \text{total caloric expenditure})/K]$, wherein when time units are in percent of an hour, J is a value selected from 1250-1290 and K is a value selected from 1610-1650. Preferred embodiments of the claimed device measure loss of fluid through the use of a pedometer and include a housing having a keyboard and a display screen, an ambient temperature sensor, an ambient humidity sensor, a step counting apparatus, a timing apparatus and a microprocessor. A fluid replacement value is communicated via a numerical display, graphic display, or both, on the display screen.

20 Claims, 4 Drawing Sheets

DEVICE AND METHOD FOR MONITORING HYDRATION STATUS

BACKGROUND

Hydration refers to the measure of water content in the body tissues. Water makes up a large proportion of the human body; approximately 60% in adult men and 55% in adult women. Almost all physiological processes are impacted by our hydration status, including regulation of body temperature and transport of oxygen and nutrients to the cells. Dehydration resulting from the failure to adequately replace fluids can lead to inadequate dissipation of heat, which may result in an elevation of core body temperature and excessive cardiovascular strain. At extreme levels of dehydration, an individual is at risk of heat exhaustion and other forms of heat-related illness. Thirst is not necessarily an accurate indicator of hydration status, as water has been found to quench the sensation of thirst before adequate body fluid replacement is achieved. Ambient temperature and humidity, as well as weight and activity level, contribute to an individual's hydration status at any given time.

The claimed device and method estimate an individual's level of hydration or dehydration based on an estimate of the person's speed of movement calculated from a measured time interval, and estimates of step count and stride length. Typical pedometers may measure distance from a user inputted stride length and may use an electronic or mechanical step counting device. Some pedometers may incorporate a timer and a user inputted body weight to estimate calories expended during activity.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

The invention relates to the operation of a daily activity monitor that provides an individualized guideline for fluid replacement during normal activity or inactivity. The claimed device measures loss of fluid through the use of a pedometer that may be worn on an individual's body or clothing or integrated into a piece of exercise equipment. Preferred embodiments of the device include a housing having a keyboard and a display screen, an ambient temperature sensor, an ambient humidity sensor, a step counting apparatus, a timing apparatus and a microprocessor. The microprocessor calculates the speed at which the user is traveling from stride length, stride count and elapsed time. Based on this speed, user inputted weight, and elapsed time, the microprocessor calculates total caloric expenditure, which it then uses to calculate fluid loss via the equation: $[(\% \text{ humidity}^2 - 1600 * \text{time})/J] + [(\text{temp } ° F. * \text{total caloric expenditure})/K]$, wherein when time is in percent of one hour, J is a value selected from 1250-1290 and K is a value selected from 1610-1650. Preferred embodiments of the claimed device communicate the fluid replacement value via a numerical display, graphic display, or both, on the display screen.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION

Figure 1:
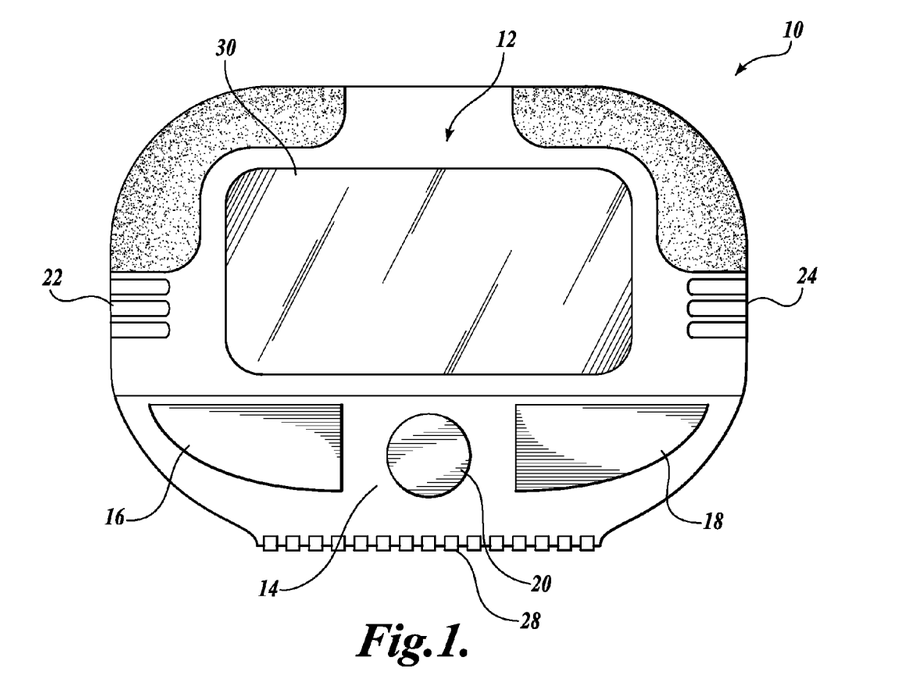
FIG. 1 is a perspective view of one embodiment of the hydration monitoring pedometer device.

FIG. 1 is a perspective view of one embodiment of the hydration monitoring pedometer device 10. A keypad 14 is located on the surface of the housing 12. The keypad 14 is comprised of a plurality of buttons including a mode button 16, a start/stop button 18 and a hydration button 20. The housing 12 also contains an ambient temperature sensor 22 and an ambient humidity sensor 24. The device may have a flip down keypad cover attached at a joint 28 to protect the buttons from inadvertent depression. A display screen 30, details of which are discussed below, is also located on the surface of the housing 12.

Figure 2A:
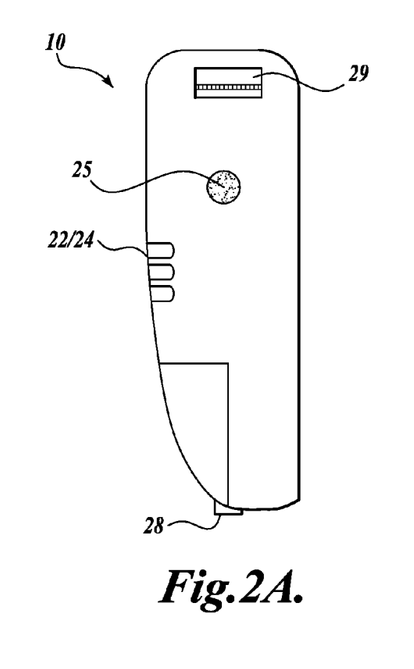
FIG. 2A is a side view of one embodiment of the hydration monitoring pedometer device.
Figure 2B:
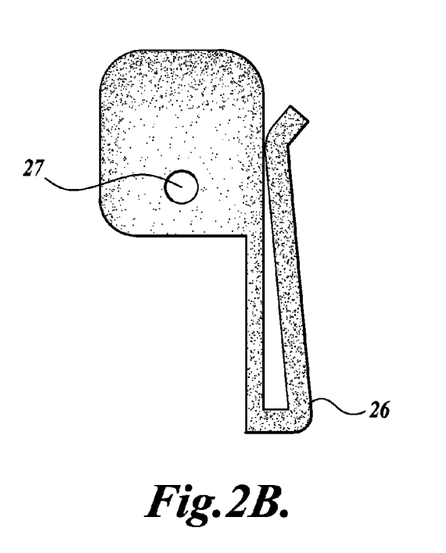
FIG. 2B is a side view of one embodiment of the clothing clip assembly of the hydration monitoring pedometer device

FIGS. 2A and 2B are side views of one embodiment of the hydration monitoring pedometer device and one embodiment of a clothing clip assembly 26. The clothing clip 26 may fasten to the housing 12 so the unit may be worn on a user's clothing or attach to a belt, fanny pack, or other accessory. Spring-loaded buttons 25 on the sides of the hydration monitoring pedometer device interlock with a clothing clip assembly 26 having corresponding button holes 27, to avoid inadvertent detachment. The device may connect to an external computer via a USB port located on the side of the device 29. Finally, a sticker (not shown) may be adhered on the back of the device providing operating instructions, illustrating a range of urine colors corresponding to various hydration levels, or providing other relevant information.

Figure 3:
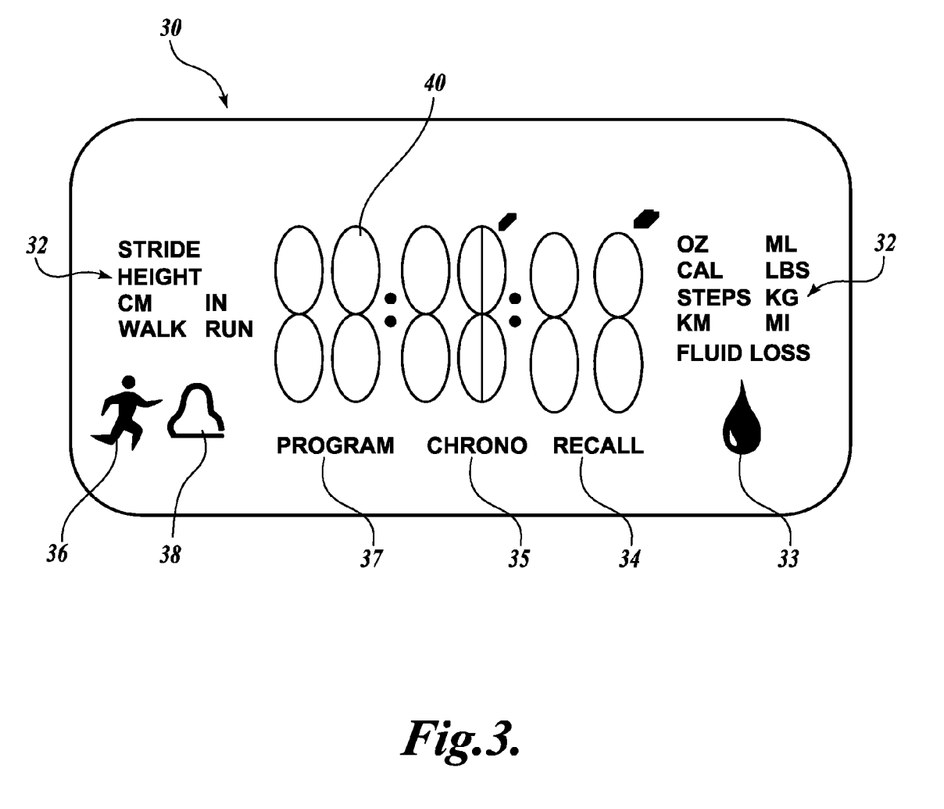
FIG. 3 is an enlarged view of the display screen of one embodiment of the hydration monitoring pedometer device.

FIG. 3 is an enlarged view of the display screen 30 of one embodiment of the hydration monitoring pedometer device. The display screen 30 may include digital numerals 40 and lettering 32 indicating the value and/or units being displayed, including stride, height, cm or in, walk or run, oz or ml, cal, lbs or kg, steps, km or mi, and fluid loss 32. The display screen 30 may also include lettering and/or graphics indicating the device is in program mode 37, chrono mode 35, 36, recall mode 34, hydration status 33 and/or that the alarm function is on/off 38.

The specific buttons and their methods of use described herein provide one embodiment of the claimed device; other combinations of buttons and/or their methods of use could be employed to achieve the device's hydration status calculation and display functions.

Programming and User Operation

One preferred embodiment of the claimed device incorporates a three-button format for ease of use. The mode 16, start/stop 18 and hydration 20 buttons may be operated by the user to: program the device; start, stop and reset the chronometer; display fluid loss, caloric expenditure, number of steps, distance and elapsed time; and to recall the last set of data collected.

When the mode button 16 is pressed once, the device is in programming mode. Pressing and holding the start/stop button 18 activates the programming sequence through which the mode button 16 is used to toggle values to the correct value, and pressing the start/stop button 18 moves the user to the next step in the sequence. The programming sequence may proceed as: a) set hours; b) set minutes; c) set whether the user wishes distance to be measured in miles or kilometers; d) set weight in pounds, if the user chose miles in step c or in kilograms if the user chose kilometers in step c, (optional); e) set height in inches if user chose miles in step c or in centimeters if the user chose kilometers in step c (optional); f) set stride length for walking (optional); g) set stride length for running (optional); h) set sex; i) set alarm on or off; and j) returns to time display. The user may opt to not enter in stride length (steps f and g) if height has been entered, as the device is capable of calculating stride length from height. Other methods of determining stride length may be employed by the device, as are discussed below.

Pressing the mode button 16 again switches the device into chrono mode. The timer starts when the start/stop button 18 is pressed and stops when it is pressed again. Once the timer has been stopped, pressing and holding the start/stop button 18 resets the device and pressing the mode button 16 switches it to recall mode, as described below.

When the timer is activated, pushing the mode button 16 switches the device to chrono-display mode and fluid loss is displayed. When fluid loss is being displayed, the user may press the hydration button 20 to toggle the fluid loss amount down. Subsequent pressings of the mode button 16 advance from the display of fluid loss to displays of calories expended, then steps, then distance and then back to the timer.

When the device is switched to recall mode, values measured over the most recent elapsed time (i.e., when the timer was most recently switched on and off) are displayed. By pressing the start/stop button 18, the user advances from elapsed time to fluid loss to caloric expenditure to steps, to distance, and then back to elapsed time. One more press of the mode button 16 returns the user to time of day.

Stride Length and Speed Adjustment

Figure 4:
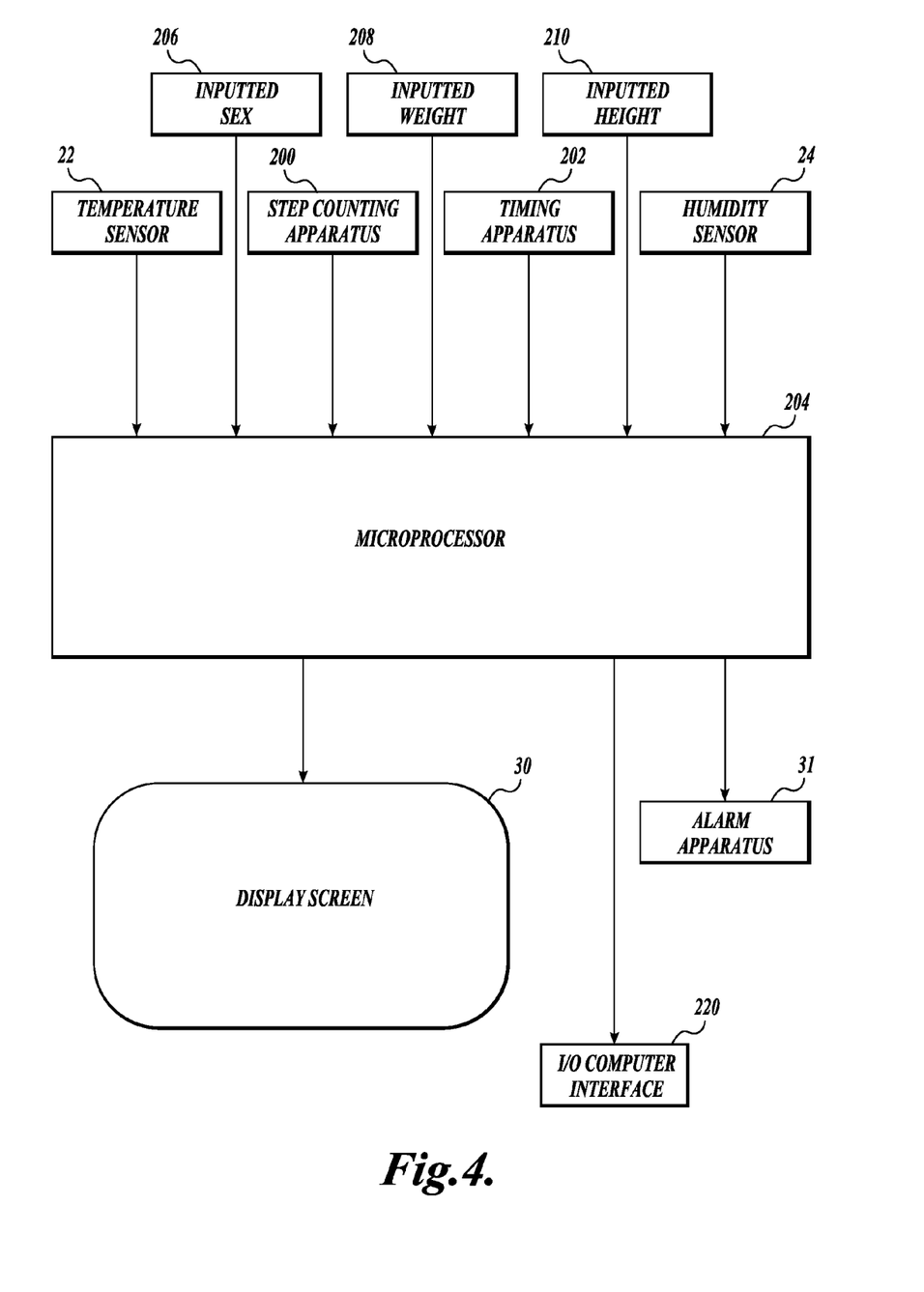
FIG. 4 is a flow diagram illustrating one embodiment of the operation of the hydration monitoring pedometer device.

FIG. 4 is a flow diagram illustrating one embodiment of the operation of the claimed device wherein the user-entered sex 206, weight 208 and height 210, along with data from the step counting apparatus 200, timing apparatus 202, temperature sensor 22 and humidity sensor 24, are input to the microprocessor 204, which, in turn, provides data to the display screen 30 and the alarm apparatus 31.

Stride length may be programmed into the device directly by the user via the mode 16 and start/stop buttons 18, as described above, or the microprocessor 204 may estimate stride length from input of the user's height using the equations: 46.1% of height while walking and 59.4% of height while running. Alternatively, the device may measure stride length directly by: 1) manual entry; 2) automated measurement wherein the user walks or runs a prescribed distance and a processor located within the pedometer divides the distance by the number of steps measured; 3) a GPS processor located within the pedometer, or 4) an in-shoe processor that calculates stride length. The step counting apparatus 200 of preferred embodiments of the claimed device may estimate number of steps via a mercury switch, a mechanical tripping mechanism, an electronic tripping mechanism, a shoe pod or a Global Positioning System (GPS).

When the device is chrono mode, the timing apparatus 202 measures elapsed time and the step counting apparatus 200 estimates the number of strides taken. This data is used by the microprocessor 204, along with a calculated stride length, to calculate speed of movement using the equation speed=distance/time. It is in the chrono mode that the device uses speed adjustment algorithms to make periodic adjustments to the stride length. Average walking speeds at which subjects performed a stride length measurement protocol, or "reference SL protocol speeds," were experimentally determined to be 101.8 meters per minute for walking and 163.5 meters per minute for running.

Figure 5:
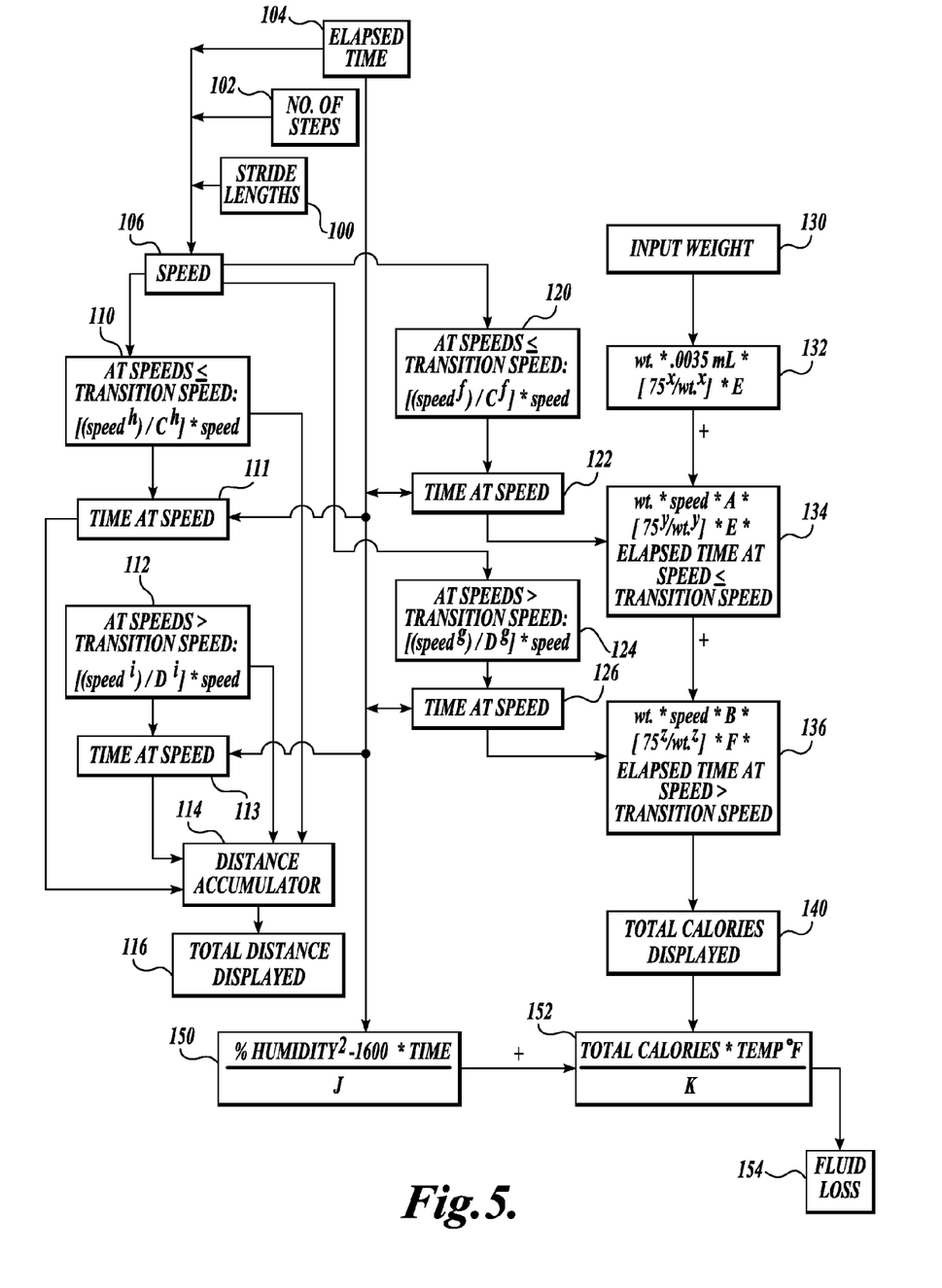
FIG. 5 is a flow diagram illustrating one embodiment of the operation of the claimed hydration status equations.

FIG. 5 is a flow diagram illustrating the hydration status equations of the claimed method and the operation of one embodiment of the claimed device. As shown in boxes 120 and 124, the speed adjustment algorithms are:

$$\text{speed}*[\text{speed}^f/C^f] \text{ for speeds} \leq \text{transition speed (120 of FIG. 5) and}$$

$$\text{speed}*[\text{speed}^g/D^g] \text{ for speeds} > \text{transition speed (124 of FIG. 5),}$$

wherein f is selected from the range 0.03-0.07 and g is selected from the range 0.31-0.35 and when speed is in meters/min, C is a value selected from the range 92-122 meters/min and D is a value selected from the range 154-174 meters/min. In one preferred embodiment, f is 0.05, g is 0.328, C is 101.8 and D is 163.5. The time at which the user spends at any given speed 122, 126, is recorded and used to calculate caloric expenditure, as is discussed below. The device may be programmed with a minimum time of movement only after which the timer records the speed, for example, 20 seconds, to avoid recordings of extraneous movements.

For the time periods spent at speeds that vary from the assumed SL protocol speeds, the user's speed is adjusted through the speed adjustment algorithms 120, 124 to account for shortening of stride length at speeds slower than the reference speeds and lengthening of stride length at speeds faster than the reference speeds. A set speed, in one preferred embodiment 107.2 meters per minute, is designated as the average speed at which a user might transition from walking-to-running. Thus, when the user is moving at speeds less than or equal to the transition speed, speed adjustment equation 120 is used. When the user is moving at speeds faster than the transition speed, speed adjustment equation 124 is used. This speed adjustment algorithm is used to calculate the user's stride length for the purposes of computing calories and, ultimately, hydration status, and differ from the equations used to calculate displayed distance due to differences in mechanical efficiency at varied walking and running speeds. No speed adjustment is necessary when stride length is measured via stride length options 3 (GPS) or 4 (In-shoe Processor) since actual stride lengths are measured when these options are employed.

Calculation of Distance

As shown in FIG. 5, the formulas used for calculating distance are:

$$\text{speed}*[\text{speed}^h/C^h] \text{ for speeds} \leq \text{transition speed (110 of FIG. 5)}$$

$$\text{speed}*[\text{speed}^i/D^i] \text{ for speeds} > \text{transition speed (112 of FIG. 5),}$$

wherein h is a value selected from 0.3-0.7 and i is a value selected from 0.4-0.8 and when speed is calculated in meters/minute, C is a value selected from the range 92-122 and D is a value selected from the range 154-174. In one preferred embodiment, h is 0.5, i is 0.6, C is 101.8 and D is 163.5. The distance formulas have a highly significant correlation (p<0.001), with an average standard error of estimate of less than 2.5% from actual distance measured during exercise. As for the speed adjustment algorithms, when the user's speed exceeds a pre-determined transition speed, in one preferred embodiment it is 107.2 meters/minute, the equation used switches from the ≦ transition speed distance equation 110 to the > transition speed distance equation 112. The elapsed time during which the user spent at various speeds is recorded 111, 113 and used to determine total accumulated distance 114. An icon on the display 30 may show a running figure or walking FIG. 36, depending on the user's speed.

Hydration Computations

Estimates of fluid loss are calculated by first determining the user's accumulated caloric expenditure over a measured time interval (130-140 of FIG. 4) and then using this value along with average temperature and average humidity over the measured time interval in a fluid loss equation (150-154 of FIG. 4). The amount of fluid lost is the fluid replacement estimate, which is displayed on the display screen 30.

a. Caloric Expenditure

Caloric expenditure over the measured time interval is the sum of basal metabolic expenditure 132 and expenditure during movement 134, 136. Movement is divided into two categories, any movement slower than a pre-determined transition speed, and movement which is faster than the transition speed. At each intensity caloric expenditure is calculated from oxygen consumption and corrected by body scaling algorithm correction factors.

Body scaling algorithm correction factors (hereinafter "correction factors") account for the effect of an individual's size on oxygen consumption to obtain a predicted or corrected parameter for the user. These correction factors are the subject of U.S. Publication No. US 2006-0090765 A1, which is incorporated herein in its entirety. In the currently claimed device, the user's estimated oxygen consumption values are adjusted in accordance with the formulas:

Oxygen consumption*[$(75)^x/(Wt)^x$] for resting

Oxygen consumption*[$(75)^y/(Wt)^y$] for speeds≦transition speed

Oxygen consumption*[$(75)^z/(Wt)^z$] for speeds>transition speed

Wherein Wt is the weight of the user, 75 kg is the weight of the reference population, x is a value selected from 0.20-0.30, y is a value selected from 0.20-0.30 and z is a value selected from 0.11-0.37. The values selected are dependent on the intensity of the user's activity. In one preferred embodiment, x is 0.25, y is 0.25 and z is 0.33. The correction factors reflect an exponential relationship between the weight of the user, the weight of the reference population which, in a preferred embodiment, is chosen to be 75 kg, and the intensity at which the person is working (x, y and z).

If the fluid loss attributable to individual differences in body dimension is not accounted for, the oxygen consumption and fluid lost by a 300-pound individual would be overestimated by an average of 16% at rest and 22% during maximal exercise, thereby putting the person at risk of hyponatremia. Correspondingly, an 80-pound person would be under-predicted by 17% at rest and 21% during maximal exercise and therefore at increased risk for dehydration.

Resting caloric expenditure is computed by first determining resting oxygen consumption and then converting that value to kilocalories (what is commonly referred to as a calorie is technically measured as one kilocalorie). Using the correspondence for a referenced sized human of 75 kg to 3.5 ml of oxygen/kg/min (which is the standard value of one resting MET or Metabolic Equivalent of Task), a true resting oxygen consumption is determined by using the correction factor exponent of 0.25 for x. Accordingly, basal caloric expenditure may be determined by the following equation (132 of FIG. 5):

$$\text{weight} * 0.0035 \text{ ml} * [75^x/\text{weight}^x] * E$$

wherein x is a value selected from 0.20-0.30 and E is a value selected from 0.0045-0.0055 kcal/ml. In one preferred embodiment, x is 0.25 and E is 0.004825 kcal/ml.

Caloric expenditure during movement at speeds less than or equal to a pre-determined transition speed, in one preferred embodiment less than or equal to 107.2 meters/minute, is determined by the equation (134 of FIG. 5):

$$\text{weight} * \text{speed of movement} * A * [75^y/\text{weight}^y]$$
$$* F * \text{elapsed time at speeds} \leq \text{pre-determined transition speed}$$

wherein A is a value selected from 0.87-0.127 ml, y is a value selected from 0.20-0.30 and F is a value selected from 0.0045-0.0055 kcal/ml. In one preferred embodiment, A is 0.107 ml, y is 0.25 and F is 0.004875 kcal/ml.

Caloric expenditures during movement at speeds greater than a pre-determined transition speed, in one preferred embodiment greater than 107.2 meters/minute, is determined by the equation (136 of FIG. 5):

$$\text{weight} * \text{speed of movement} * B * [75^z/\text{weight}^z]$$
$$* G * \text{elapsed time at speeds} > \text{pre-determined transition speed}$$

wherein B is a value selected from 0.154-0.194 ml, z is a value selected from 0.11-0.37 and F is a value selected from 0.0045-0.0055 kcal/ml. In one preferred embodiment, B is 0.174 ml, z is 0.328 and G is 0.005 kcal/ml.

In all three of the caloric expenditure equations 132, 134 and 136, once the user's speed is determined, it is multiplied to an estimated value of oxygen consumed per weight basis (0.0035 ml in equation 132, A in equation 134 and B in equation 136). This number is then corrected for the body dimensions of the user as discussed above. The oxygen consumed per weight values in one preferred embodiment are 0.107 ml of oxygen consumed per meter/min of speed attained for speeds slower than or equal to the transition speed and 0.174 ml of oxygen consumed per meter/min of speed attained for speeds greater than the transition speed. These values were derived from original metabolic research on a diverse group of subjects corresponding to the U.S. weighted mean weight of 75 kg (165 lbs).

The caloric expenditure equations account for typical non-protein RER (Respiratory Exchange Ratios) ratios and calculate the contribution of kilocalories derived from the computed oxygen consumptions. Typical non-protein RER values range from 4.686 kcal per liter of oxygen consumed to 5.047 kcal per liter of oxygen consumed. Typical but not limiting values for resting metabolism are 0.0045-0.0055 and preferably 0.004825 (RER of 0.82) produced per ml of oxygen consumed at rest (E in 132 of FIG. 5), 0.0045-0.0055 and preferably 0.004875, (RER of 0.86) kcal/ml while walking (F in 134 of FIG. 5) and 0045-0.0055 and preferably 0.00500 (RER 0.96) kcal/ml while running (G of 136 of FIG. 5). After total calories for the time period in which the device was in chrono mode are computed, they are used to compute fluid loss. The caloric expenditure may also be displayed on the display screen 30.

In one embodiment of the claimed device, if the user enters female during programming, the resting and ≦ transition speed caloric expenditure equations 132, 134 are multiplied by 0.73 to account for the hormonal differences and inherently greater body fat to lean tissue ratio typical of females. This variation does not have an effect on caloric expenditure during running, so no adjustment is necessary for the > transition speed equation 136.

b.) Fluid Loss/Fluid Replacement Estimate

Preferred embodiments of the claimed device may integrate humidity 22 and temperature sensors 24 and/or allow user input of temperature and/or humidity. Ambient air temperature and humidity are used to compute the fluid loss/fluid replacement estimate via the equation (150, 152, 154 of FIG. 5):

$$\{[(\% \text{ humidity}^2 - 1600)*\text{time}]/J\} + [(\text{temp }°\text{F.}*\text{total caloric expenditure})/K]$$

wherein when time units are in % of an hour, J is a value selected from 1250-1290 and K is a value selected from 1610-1650. In a preferred embodiment, when time is in percent of an hour (minutes/60), and total caloric expenditure is in kcals, J is 1270 and K is 1630 thereby giving the equation:

$$\{[(\% \text{ humidity}^2 - 1600)*\text{total time in min}/60]/1270\} + [(\text{temp }°\text{F.}*\text{total caloric expenditure in kcal})/1630] = \text{fluid loss/fluid replacement estimate in ounces.}$$

The fluid loss/fluid replacement estimate can be converted to milliliters by the conversion factor of 29.57 milliliters=one ounce.

The device may include an alarm apparatus 31 to notify the user of a fluid need exceeding a specified percentage of his or her body weight and, preferably, exceeding 1.5% of his or her body weight as this is the level beyond which a loss in performance is inevitable in most instances. The hydration alarm 31 may be engaged or disengaged at the user's option and when the alarm is on, a graphic 38 may appear on the display screen 30. In addition, a graphic indicator of hydration status, such as a water bottle or a drop of water 33, may also appear on the display screen 30. Embodiments of the claimed device may be programmed with a low humidity default value of 50% and a low temperature default value of 60° F. When humidity and/or temperature measurements taken by the sensors are lower than these default values, the default values may be used.

While the claimed device is in chrono mode, the user may depress and hold the hydration button 20 to set the fluid loss level back zero if he or she has consumed the total fluid replacement requirement, or may toggle down the amount of fluid at set intervals, preferably 0.10 oz or 1.0 ml, to a value greater than zero. The device will then resume calculations starting from 0 or the new, decreased level. For example, the device may indicate that the user has lost 4 oz. He drinks 2 oz. and, with the device still in chrono mode, toggles the hydration button until the value reads 2 oz., after which he keeps on running. The device resumes calculations starting at the 2 oz level.

Preferred embodiments of the claimed device and method may calculate fluid replacement estimates throughout a 24-hour period including periods of inactivity, exercise and sleep. Fluid replacement needs for all individuals from the sedentary to the extremely active are accurately estimated and the device compensates, through the body scaling equations, for any extreme in body dimension. Just as hydration status during an exercise bout may be estimated, the hydration status of a bedridden patient in a hospital setting may also be monitored. As such, the claimed device and method are not limited to estimating hydration in an athlete or only in the performance of physical exercise.

Method for Monitoring Hydration

When stride length, elapsed time, stride count, ambient humidity, ambient temperature and weight are provided, a method for estimating the user's level of hydration includes select steps as described above. Specifically, stride length (100 of FIG. 5) and elapsed time (104 of FIG. 5) are used to calculate speed of movement (106 of FIG. 5). Speed of movement is then used to calculate total caloric expenditure for a given duration (140 of FIG. 5). Fluid Loss (154 of FIG. 5) is then determined using the equation:

$$\{[(\% \text{ humidity}^2 - 1600)*\text{time}]/J\} + [(\text{temp }°\text{F.}*\text{total caloric expenditure})/K],$$

(150, 152 of FIG. 5) and wherein when time units are in percent of an hour, J is a value selected from 1250-1290 and K is a value selected from 1610-1650. Also as described above, total caloric expenditure for a given duration is calculated from speed of movement using the equation:

$$\text{weight}*0.0035 \text{ ml}*[(75)^x/\text{weight}^x]*E +$$

$$\text{weight}*\text{speed of movement}*A*[75^y/\text{weight}^y]$$
$$*F*\text{accumulated time at speeds slower than or equal to a walking-to-running transition speed} +$$

$$\text{weight}*\text{speed of movement}*B*[75^z/\text{weight}^z]$$
$$*G*\text{accumulated time at transition speeds slower than or equal to a walking-to-running transition speed,}$$

(132, 134, 136 of FIG. 5) wherein x is a value selected from 0.20-0.30, y is a value selected from 0.20-0.30 and z is a value selected from 0.11-0.37 and when weight is in kg and speed is in meters/min., A is a value selected from 0.87-0.127 ml, B is a value selected from 0.160-0.200 ml, E is a value selected from 0.0045-0.0055 kcal/ml, F is a value selected from 0.0045-0.0055 kcal/ml, and G is a value selected from 0.0045-0.0055 kcal/ml.

Preferred embodiments of the claimed method may also incorporate speed adjustment algorithms wherein speed of movement is periodically adjusted using the equations:

$$\text{speed}*[\text{speed}^f/C^f] \text{ for speeds} \leq \text{walking-to-running transition speed (120 of FIG. 5)}$$

and $$\text{speed}*[\text{speed}^g/D^g] \text{ for speeds} > \text{walking-to-running transition speed (124 of FIG. 5),}$$

wherein f is selected from the range 0.03-0.07 and g is selected from the range 0.31-0.35 and when speed is in meters/min, C is a value selected from the range 92-122 meters/min and D is a value selected from the range 154-174 meters/min. In one preferred embodiment, f is 0.05, g is 0.328, C is 101.8 and D is 163.5.

While illustrative embodiments have been illustrated and described, it will be appreciated that various changes can be made therein without departing from the spirit and scope of the invention.

The invention claimed is:

1. A fluid loss monitoring pedometer device, comprising:
   a) a housing having a keyboard and a display screen;
   b) an ambient temperature sensor;
   c) an ambient humidity sensor;
   d) a stride counting apparatus;
   e) a timing apparatus; and f) a microprocessor;

wherein the microprocessor calculates speed of movement from stride count, stride length and elapsed time; and wherein speed of movement is used by the microprocessor to calculate total caloric expenditure for a given duration; and wherein the microprocessor uses total caloric expenditure to calculate fluid loss using the equation:

$$\{[(\% \text{ humidity}^2-1600)*\text{time}]/J\}+[(\text{temp }°\text{F.}*\text{total caloric expenditure})/K];$$

wherein time units are in percent of an hour, J is a value selected from 1250-1290 and K is a value selected from 1610-1650; and wherein the display screen indicates the calculated fluid loss.

2. The device of claim 1, wherein speed of movement is used by the microprocessor to calculate total caloric expenditure for a given duration using the equation:

$$\text{weight}*0.0035 \text{ ml}*[(75)^x/\text{weight}^x]*E+$$

$$\text{weight}*\text{speed of movement}*A*[75^y/\text{weight}^y]$$
$$*F*\text{accumulated time at speeds slower than or equal to a walking-to-running transition speed}+$$

$$\text{weight}*\text{speed of movement}*B*[75^z/\text{weight}^z]$$
$$*G*\text{accumulated time at speeds faster than a walking-to-running transition speed,}$$

wherein x is a value selected from 0.20-0.30, y is a value selected from 0.20-0.30 and z is a value selected from 0.11-0.37 and when weight is in kg and speed is in meters/min., A is a value selected from 0.87-0.127 ml, B is a value selected from 0.160-0.200 ml, E is a value selected from 0.0045-0.0055 kcal/ml, F is a value selected from 0.0045-0.0055 kcal/ml, and G is a value selected from 0.0045-0.0055 kcal/ml.

3. The device of claim 2, wherein x is 0.25, y is 0.25 and z is 0.33 and when weight is in kg and speed is in meters/min., A is 0.107 ml and B is 0.174 ml, E is 0.004825 kcal/ml, F is 0.004875 kcal/ml and G is 0.005 kcal/ml.

4. The device of claim 1, wherein the step counting apparatus is selected from a mercury switch, a mechanical tripping mechanism, an electronic tripping mechanism, a shoe pod, or a Global Positioning System.

5. The device of claim 1, wherein the microprocessor is adapted to estimate stride length from an input of the user's height as 46.1% of the input height for a walking stride length, and 59.4% of the input height for a running stride length.

6. The device of claim 1, wherein the calculated fluid loss may be adjusted by the user, after which the calculated fluid loss includes the adjustment to the calculated fluid loss.

7. The device of claim 1, wherein the microprocessor includes an alarm function which may be activated by the user to sound when the user attains a total fluid deficit of 1.5% of body weight.

8. The device of claim 1, wherein if the user indicates sex as female, the microprocessor calculates total caloric expenditure for a given duration using the equation:

$$\text{weight (kg)}*0.0035 \text{ ml}*[(75)^x/(\text{weight (kg)})^x]*4.875 \text{ kcal/L}*0.73+$$

$$\text{weight (kg)}*\text{speed of movement (meters/min)}*A \text{ ml}*$$
$$[(75)^y/(\text{weight (kg)})^y]*0.004875 \text{ kcal/ml}*\text{minutes}$$
$$\text{of accumulated time at transition speeds slower}$$
$$\text{than or equal to a walking-to-running transition}$$
$$\text{speed}*0.73+$$

$$\text{weight (kg)}*\text{speed of movement (meters/min)}*B \text{ ml}*$$
$$[(75)^z/(\text{weight (kg)})^z]*0.0050 \text{ kcal/ml}*\text{minutes of}$$
accumulated time at transition speeds faster than a walking-to-running transition speed;

wherein x is a value selected from 0.20-0.30, y is a value selected from 0.20-0.30 and z is a value selected from 0.11-0.37 and wherein A is a value selected from 0.87-0.127 ml and B is a value selected from 0.160-0.200 ml.

9. A fluid loss monitoring pedometer device, comprising:
a) a housing having a keyboard and a display;
b) an ambient temperature sensor,
c) an ambient humidity sensor;
d) a stride counting apparatus;
e) a timing apparatus;
f) a microprocessor; and wherein the microprocessor calculates speed of movement from stride count, stride length and elapsed time; and wherein the microprocessor periodically adjusts speed of movement according to the speed adjustment equations:

$$\text{speed}*[\text{speed}^f/C^f] \text{ for walking and}$$

$$\text{speed}*[\text{speed}^g/D^g] \text{ for running,}$$

wherein f is selected from the range 0.03-0.07, g is selected from the range 0.31-0.35, speed is in meter/min, C is a value selected from the range 92-122 meters/min and D is a value selected from the range 154-174 meters/min;

wherein speed of movement is used by the microprocessor to calculate total caloric expenditure for a given duration; and wherein the microprocessor uses total caloric expenditure to calculate fluid loss using the equation:

$$\{[(\% \text{ humidity}^2-600)*\text{time}]/J\}+[(\text{temp }°\text{F.}*\text{total caloric expenditure})/K];$$

wherein time units are in percent of an hour, J is a value selected from 1250-1290 and K is a value selected from 1610-1650; and wherein the display screen indicates the calculated fluid loss.

10. The device of claim 9, wherein f is 0.05 and g is 0.328, and wherein when speed is in meters/minute, C is 101.8, D is 163.5, J is 1270 and K is 1630.

11. The device of claim 9, wherein the speed adjustment equations are based on a walking reference speed of 101.8 meters per minute and a running reference speed of 163.5 meters per minute and wherein for the time periods spent at speeds that vary from the assumed speeds, speeds are adjusted to account for shortening of stride length at slower than reference speeds and lengthening of stride length at faster than reference speeds.

12. The device of claim 9, wherein the step counting apparatus is selected from a mercury switch, a mechanical tripping mechanism, an electronic tripping mechanism, a shoe pod, or a Global Positioning System.

13. The device of claim 9, wherein the calculated fluid loss may be adjusted by the user, after which the calculated fluid loss incorporates the adjustment to the calculated fluid loss.

14. The device of claim 9, wherein the microprocessor includes an alarm function which may be activated by the user to sound when the user attains a total fluid deficit of 1.5% of body weight.

15. A pedometer device, comprising:
a) a housing having a keyboard and a display;
b) an ambient temperature sensor;
c) an ambient humidity sensor;
d) a step counting apparatus;
a timing apparatus;

f) a microprocessor; and wherein the microprocessor calculates speed of movement from stride count, stride length, and elapsed time; and wherein the microprocessor calculates and displays distance from speed and elapsed time using the equation:

$$\text{speed}*[\text{speed}^h/C^h]*\text{minutes of accumulated time at speeds slower than or equal to a walking-to-running transition speed}+$$

$$\text{speed}*[\text{speed}^i/D^i]*\text{minutes of accumulated time at speeds faster than a walking-to-running transition speed};$$

wherein h is a value selected from 0.3-0.7, i is a value selected from 0.4-0.8, speed is in meters/minute, C is a value selected from the range 92-122 meters/min and D is a value selected from the range 154-174 meters/min; and wherein speed of movement is used by the microprocessor to calculate total accumulated distance.

16. The device of claim 15, wherein h is 0.5, i is 0.6, and wherein when speed is in meters/minute, C is 101.8, D is 163.5, J is 1270 and K is 1630.

17. The device of claim 15, wherein the microprocessor is adapted to estimate stride length from an input of the user's height as 46.1% of the input height if speed is slower than or equal to 107.2 meters per minute, and 59.4% of the input height if speed is faster than 107.2 meters per minute.

18. A method for monitoring fluid loss comprising the steps of:

a) providing stride length, elapsed time, stride count, ambient humidity, ambient temperature and weight;

b) calculating speed of movement from stride length, stride count, and elapsed time;

c) calculating total caloric expenditure for a given duration from speed of movement;

d) calculating fluid loss using the equation:

$$\{[(\% \text{ humidity}^2-1600)*\text{time}]/J\}+[(\text{temp }°\text{F.}*\text{total caloric expenditure})/K];$$

wherein time units are in percent of an hour, J is a value selected from 1250-1290 and K is a value selected from 1610-1650; and e) indicating the calculated fluid loss.

19. The method of claim 18, wherein speed of movement is used to calculate total caloric expenditure for a given duration using the equation:

$$\text{weight}*0.0035 \text{ ml}*[(75)^x/\text{weight}^x]*E+$$

$$\text{weight}*\text{speed of movement}*A*[75^y/\text{weight}^y]$$
$$*F*\text{accumulated time at speeds slower than or equal to a walking-to-running transition speed}+$$

$$\text{weight}*\text{speed of movement}*B*[75^z/\text{weight}^z]$$
$$*G*\text{accumulated time at speeds faster than a walking-to-running transition speed},$$

wherein x is a value selected from 0.20-0.30, y is a value selected from 0.20-0.30 and z is a value selected from 0.11-0.37 and when weight is in kg and speed is in meters/min., A is a value selected from 0.87-0.127 ml, B is a value selected from 0.160-0.200 ml, E is a value selected from 0.0045-0.0055 kcal/ml, F is a value selected from 0.0045-0.0055 kcal/ml, and G is a value selected from 0.0045-0.0055 kcal/ml.

20. The method of claim 18, wherein speed of movement is periodically adjusted using the equations:

$$\text{speed}*[\text{speed}^f/C^f] \text{ for speeds} \leq \text{walking-to-running transition speed and}$$

$$\text{speed}*[\text{speed}^g/D^g] \text{ for speeds} > \text{walking-to-running transition speed}$$

wherein f is selected from the range 0.03-0.07, g is selected from the range 0.31-0.35, speed is in meters/min, C is a value selected from the range 92-122 meters/min and D is a value selected from the range 154-174 meters/min.

* * * * *

UNITED STATES PATENT AND TRADEMARK OFFICE
CERTIFICATE OF CORRECTION

PATENT NO. : 7,493,232 B1
APPLICATION NO. : 11/846414
DATED : February 17, 2009
INVENTOR(S) : B. J. Surina It is certified that error appears in the above-identified patent and that said Letters Patent is hereby corrected as shown below:

| COLUMN | LINE | ERROR |
|---|---|---|
| 10 (Claim 9, | 32 line 24) | "$\{[(\%humidity2-600) * time]/J\} + [(temp\ °F * total\ caloric\ expenditure)/K];$" should read --$\{[(\%humidity2-1600) * time]/J\} + [(temp\ °F * total\ caloric\ expenditure)/K];$-- |
| 10 (Claim 15, | 67 line 6) | before "a timing apparatus;" insert --e)-- |

Signed and Sealed this

Twenty-eighth Day of July, 2009

JOHN DOLL
*Acting Director of the United States Patent and Trademark Office*